US010195023B2

(12) United States Patent
Wrobel

(10) Patent No.: US 10,195,023 B2
(45) Date of Patent: Feb. 5, 2019

(54) PROSTHETIC HEART VALVES INCLUDING PRE-STRESSED FIBERS

(71) Applicant: Boston Scientific SciMed, Inc., Maple Grove, MN (US)

(72) Inventor: Thomas A. Wrobel, Long Lake, MN (US)

(73) Assignee: Boston Scientific Scimed, Inc., Maple Grove, MN (US)

(*) Notice: Subject to any disclaimer, the term of this patent is extended or adjusted under 35 U.S.C. 154(b) by 22 days.

(21) Appl. No.: 15/257,211

(22) Filed: Sep. 6, 2016

(65) Prior Publication Data

US 2017/0071729 A1 Mar. 16, 2017

Related U.S. Application Data

(60) Provisional application No. 62/218,776, filed on Sep. 15, 2015.

(51) Int. Cl.
*A61F 2/24* (2006.01)

(52) U.S. Cl.
CPC .......... *A61F 2/2415* (2013.01); *A61F 2/2412* (2013.01); *A61F 2/2418* (2013.01); *A61F 2210/0076* (2013.01); *A61F 2310/00023* (2013.01)

(58) Field of Classification Search
CPC ........ A61F 2/24; A61F 2/2415; A61F 2/2412; A61F 2/2418
See application file for complete search history.

(56) References Cited

U.S. PATENT DOCUMENTS

| 4,016,714 | A | 4/1977 | Crandall |
| 4,340,091 | A | 7/1982 | Davis et al. |
| 4,753,652 | A | 6/1988 | Langer et al. |
| 5,296,292 | A | 3/1994 | Butters |
| 5,688,597 | A | 11/1997 | Kohno |
| 5,740,051 | A | 4/1998 | Sanders, Jr. et al. |
| 6,165,215 | A | 12/2000 | Rottenberg et al. |
| 6,726,715 | B2* | 4/2004 | Sutherland ............ A61F 2/2412 623/2.1 |
| 7,335,264 | B2 | 2/2008 | Austin et al. |
| 7,517,353 | B2 | 4/2009 | Weber |
| 7,521,296 | B2 | 4/2009 | Wood et al. |
| 7,615,335 | B2 | 11/2009 | Shelnut et al. |

(Continued)

FOREIGN PATENT DOCUMENTS

| CN | 1449266 | 10/2003 |
| CN | 104780952 | 7/2015 |

(Continued)

OTHER PUBLICATIONS

"Decision of Final Rejection," for China Patent Application No. 201380044842.0, dated Apr. 7, 2017 (18 pages) with Summary.

(Continued)

*Primary Examiner* — Jason-Dennis Stewart
(74) *Attorney, Agent, or Firm* — Pauly, DeVries Smith & Deffner LLC

(57) ABSTRACT

A prosthetic heart valve includes a base and one or more heart valve leaflets. At least a portion of the leaflet including a composite material that contains a polymer substrate and a pre-stressed reinforcement element at least partially disposed in the polymer substrate.

13 Claims, 8 Drawing Sheets

(56) References Cited

U.S. PATENT DOCUMENTS

| | | | |
|---|---|---|---|
| 7,786,670 | B2 | 8/2010 | Veres et al. |
| 7,988,900 | B2 | 8/2011 | Beith et al. |
| 8,324,290 | B2 | 12/2012 | Desai et al. |
| 8,590,747 | B2 | 11/2013 | Keller et al. |
| 8,845,580 | B2 | 9/2014 | Gellman et al. |
| 8,864,816 | B2 | 10/2014 | Flanagan et al. |
| 9,056,006 | B2 | 6/2015 | Edelman et al. |
| 9,074,318 | B2 | 7/2015 | Chou et al. |
| 9,554,900 | B2 | 1/2017 | Bruchman et al. |
| 9,814,572 | B2 | 11/2017 | Edelman et al. |
| 2001/0025196 | A1 | 9/2001 | Chinn et al. |
| 2002/0082689 | A1 | 6/2002 | Chinn et al. |
| 2003/0055496 | A1 | 3/2003 | Cai et al. |
| 2003/0078652 | A1 | 4/2003 | Sutherland et al. |
| 2003/0097175 | A1 | 5/2003 | O'connor et al. |
| 2003/0171802 | A1 | 9/2003 | Wilder et al. |
| 2003/0183982 | A1 | 10/2003 | Jansen et al. |
| 2004/0015233 | A1 | 1/2004 | Jansen et al. |
| 2004/0022939 | A1 | 2/2004 | Kim et al. |
| 2005/0228486 | A1 | 10/2005 | Flagle et al. |
| 2006/0190074 | A1 | 8/2006 | Hill et al. |
| 2007/0118210 | A1 | 5/2007 | Pinchuk et al. |
| 2007/0144124 | A1 | 6/2007 | Schewe et al. |
| 2007/0232169 | A1 | 10/2007 | Strickler et al. |
| 2008/0045420 | A1 | 2/2008 | Karagianni et al. |
| 2009/0041978 | A1 | 2/2009 | Sogard et al. |
| 2009/0054969 | A1 | 2/2009 | Salahieh et al. |
| 2009/0117334 | A1* | 5/2009 | Sogard .................. A61F 2/2412 428/156 |
| 2010/0023104 | A1 | 1/2010 | Desai et al. |
| 2010/0179298 | A1 | 7/2010 | Faust et al. |
| 2010/0249922 | A1* | 9/2010 | Li ........................ A61F 2/2412 623/2.17 |
| 2011/0022160 | A1 | 1/2011 | Flanagan et al. |
| 2011/0208299 | A1 | 8/2011 | Marissen et al. |
| 2013/0150957 | A1 | 6/2013 | Weber et al. |
| 2013/0211508 | A1 | 8/2013 | Lane et al. |
| 2013/0274874 | A1* | 10/2013 | Hammer ............... A61F 2/2412 623/2.19 |
| 2014/0005771 | A1 | 1/2014 | Braido et al. |
| 2014/0005772 | A1 | 1/2014 | Edelman et al. |
| 2014/0018440 | A1 | 1/2014 | Boden et al. |
| 2014/0088716 | A1* | 3/2014 | Zubok ...................... A61F 2/30 623/18.11 |
| 2014/0163671 | A1 | 6/2014 | Bruchman et al. |
| 2014/0180402 | A1 | 6/2014 | Bruchman et al. |
| 2014/0322512 | A1 | 10/2014 | Pham et al. |
| 2015/0182332 | A1 | 7/2015 | Edelman et al. |
| 2015/0265392 | A1* | 9/2015 | Flanagan ................. A61F 2/04 623/23.65 |
| 2016/0296322 | A1 | 10/2016 | Edelman |
| 2016/0296323 | A1 | 10/2016 | Wulfman et al. |
| 2016/0296325 | A1 | 10/2016 | Edelman |
| 2017/0000610 | A1 | 1/2017 | Eppihimer et al. |
| 2017/0014227 | A1 | 1/2017 | Boden et al. |
| 2017/0333185 | A1 | 11/2017 | Weber et al. |
| 2018/0049869 | A1 | 2/2018 | Edelman et al. |

FOREIGN PATENT DOCUMENTS

| | | |
|---|---|---|
| JP | H0654868 | 3/1994 |
| WO | 0224119 | 3/2002 |
| WO | 02074201 | 9/2002 |
| WO | 2006000763 | 1/2006 |
| WO | 2008097592 | 8/2008 |
| WO | 2009038761 | 3/2009 |
| WO | 2010020660 | 2/2010 |
| WO | 2010048281 | 4/2010 |
| WO | 2014008207 | 1/2014 |
| WO | 2014143866 | 9/2014 |
| WO | 2014149319 | 9/2014 |
| WO | 2016164197 | 10/2016 |
| WO | 2016164209 | 10/2016 |
| WO | 2017004035 | 1/2017 |
| WO | 2017011392 | 1/2017 |
| WO | 2017048575 | 3/2017 |
| WO | 2017200920 | 11/2017 |

OTHER PUBLICATIONS

"International Preliminary Report on Patentability," for PCT Application No. PCT/US2016/024614 dated Oct. 19, 2017 (7 pages).
"International Preliminary Report on Patentability," for PCT Application No. PCT/US2016/024753 dated Oct. 19, 2017 (7 pages).
"International Preliminary Report on Patentability," for PCT Application No. PCT/US2016/039808 dated Jan. 11, 2018 (8 pages).
"International Preliminary Report on Patentability," for PCT Application No. PCT/US2016/041757 dated Jan. 25, 2018 (8 pages).
"Non-Final Office Action," for U.S. Appl. No. 15/193,794 dated Mar. 14, 2018 (14 pages).
"Non-Final Office Action," for U.S. Appl. No. 15/193,794 dated Nov. 6, 2017 (32 pages).
"Response to Non-Final Office Action," for U.S. Appl. No. 14/656,044 dated Mar. 17, 2017 and filed with the USPTO Jun. 8, 2017 (11 pages).
"Response to Non-Final Office Action," for U.S. Appl. No. 15/193,794, dated Nov. 6, 2017 and filed with the USPTO Feb. 13, 2018 (7 pages).
Aksoy, Ayse E. et al., "Surface Modification of Polyurethanes with Covalent Immobilization of Heparin," Macromolecular Symposia, vol. 269, Issue 1, pp. 145-153, Aug. 2008 (9 pages).
Alferiev, Ivan et al., "Prevention of polyurethane valve cusp calcification with covalently attached bisphosphonate diethylamino moieties," J Biomed Mater Res 66A: 385-395, 2003 (11 pages).
Athappan, Ganesh et al., "Influence of Transcatheter Aortic Valve Replacement Strategy and Valve Design on Stroke After Transcatheter Aortic Valve Replacement: A Meta-Analysis and Systematic Review of Literature," J Am Coll Cardiol. 2014;63(20):2101-2110 (10 pages).
Barkoula, Nektaria-Marianthi et al., "Processing of Single Polymer Composites Using the Concept of Constrained Fibers," Polymer Composites, 2005, 26: p. 114-120 (7 pages).
Bastiaansen, Cees W. et al., "Melting Behavior of Gelspun-Drawn Polyolefins," Makromol. Chem., Macromol. Symp., 1989. 28: p. 73-84 (12 pages).
Bates, Frank S. et al., "Multiblock Polymers: Panacea or Pandora's Box?" Science, 2012, 336:434-440 (7 pages).
Bernacca, Gillian M. et al., "Mechanical and morphological study of biostable polyurethane heart valve leaflets explanted from sheep," J Biomed Mater Res 61:138-145, 2002 (8 pages).
Bhattacharyya, D. et al., "Polyamide 6 single polymer composites," eXPRESS Polym. Lett., 2009. 3(8): p. 525-532 (8 pages).
Cacciola, G. et al., "A Synthetic Fiber-Reinforced Stentless Heart Valve," Journal of Biomechanics, Jan. 1, 2000, pp. 653-658, XP055284947, Retrieved from the Internet: URL:http://ac.els-cdn.com. (6 pages).
Cacciola, G. et al., "A Three-Dimesional Mechanical Analysis of a Stentless Fibre-Reinforced Aortic Valve Prosthesis," Journal of Biomechanics, Jan. 1, 2000, pp. 521-530, XP055284955, Retrieved from the Internet: URL:http://ac.els-cdn.com. (10 pages).
Charles, Lyndon F. et al., "Self-reinforced composites of hydroxyapatite-coated PLLA fibers: fabrication and mechanical characterization," J. Mech. Behav. Biomed. Mater., 2013. 17: p. 269-277 (9 pages).
Claiborne, Thomas E. et al., "In Vitro Evaluation of a Novel Hemodynamically Optimized Trileaflet Polymeric Prosthetic Heart Valve," Journal of Biomechanical Engineering 2013, vol. 135 (8 pages).
"Communication Pursuant to Article 94(3) EPC," for European Patent Application No. 13739321.1 dated Sep. 8, 2016 (4 pages).
"Communication Pursuant to Rules 161(1) and 162 EPC," for EP Patent Application No. 13739321.1-1455 dated Feb. 18, 2015 (2 pages).
De Yoreo, James J. et al., "Principles of Crystal Nucleation and Growth," Biomineralization, Mineral Soc. Am., Washington, DC, 2003, pp. 57-93 (37 pages).

(56) References Cited

OTHER PUBLICATIONS

Dencheva, Nadya et al., "Structure-properties relationship in single polymer composites based on polyamide 6 prepared by in-mold anionic polymerization," J. Mater. Sci., 2013. 48(20): p. 7260-7273 (14 pages).
Duhovic, Miro P. et al., "Polyamide 66 polymorphic single polymer composites," Open Macromol. J., 2009. 3: p. 37-40. (4 pages).
Fakirov, Stoyko "Nano- and Microfibrillar Single-Polymer Composites: A Review," Macromol. Mater. Eng., 2013. 298(1): p. 9-32 (24 pages).
Feng, Yakai et al., "Surface modification of polycarbonate urethane by covalent linkage of heparin with a PEG spacer," Transactions of Tianjin University, Feb. 2013, vol. 19, Issue 1, pp. 58-65 (8 pages).
File History for Related U.S. Appl. No. 14/656,044 downloaded Nov. 14, 2016 (386 pages).
File History for Related U.S. Appl. No. 13/932,968 downloaded Nov. 14, 2016 (431 pages).
"First Office Action," for Chinese Patent Application No. 201380044842.0 dated Dec. 18, 2015 (15 pages) with English Translation.
Gallocher, "Durability Assessment of Polymer Trileaflet Heart Valves," FIU Electronic Theses and Dissertations, Paper 54, 2007 (237 pages).
Généreux, Philippe et al., "Vascular Complications After Transcatheter Aortic Valve Replacement: Insights from the PARTNER Trial," J Am Coll Cardiol. 2012;60(12):1043-1052 (10 pages).
"Glycosaminoglycan," Wikipedia, posted on or before Oct. 16, 2004, retrieved Feb. 13, 2014, http://en.wikipedia.org/wiki/Glycosaminoglycan, 6 pages.
Gong, Ying et al., "Polyamide single polymer composites prepared via in situ anionic polymerization of ε-caprolactam," Composites, Part A, 2010. 41A(8): p. 1006-1011 (6 pages).
Gong, Ying et al., "Single polymer composites by partially melting recycled polyamide 6 fibers: preparation and characterization," J. Appl. Polym. Sci., 2010. 118(6): p. 3357-3363 (7 pages).
Goyal, R. K. et al., "High performance polymer composites on PEEK reinforced with aluminum oxide," J. Appl. Polym. Sci., 2006. 100(6): p. 4623-4631 (9 pages).
Han, Dong K. et al., "In vivo biostability and calcification-resistance of surface-modified PU-PEO-SO3," Journal of Biomedical Materials Research, vol. 27, 1063-1073, 1993 (11 pages).
Hine, P.J. et al., "High stiffness and high impact strength polymer composites by hot compaction of oriented fibers and tapes.," in Mechanical Properties of Polymers Based on Nanostructure and Morphology, CRC Press, 2005 (45 pages).
Hine, P.J. et al., "Hot compaction of woven nylon 6,6 multifilaments," J. Appl. Polym. Sci., 2006. 101(2): p. 991-997 (7 pages).
Hine, P.J. et al., "Hot Compaction of Woven Poly(ethylene terephthalate) Multifilaments," J. Appl. Polym. Sci., 2004. 91(4): p. 2223-2233 (11 pages).
Hine, P.J. et al., "Hybrid carbon fibre/nylon 12 single polymer composites," Composites Part A: Applied Science and Manufacturing 65 (2014) (17 pages).
"International Preliminary Report on Patentability," for International Application No. PCT/US2013/048976 dated Jan. 6, 2015 (9 pages).
"International Search Report & Written Opinion," for International Application No. PCT/US2013/048976, dated Nov. 19, 2013 (20 pages).
"International Search Report and Written Opinion," for PCT Application No. PCT/US2016/041757 dated Oct. 12, 2016 (12 pages).
"International Search Report and Written Opinion," for PCT/US2016/024614 dated Jul. 12, 2016 (13 pages).
"International Search Report and Written Opinion," for PCT/US2016/024753 dated Jul. 22, 2016 (11 pages).
"International Search Report and Written Opinion," for PCT/US2016/039808 dated Sep. 26, 2016 (11 pages).
Jiang, Shaoyi et al., "Ultralow-Fouling, Functionalizable, and Hydrolyzable Zwitterionic Materials and Their Derivatives for Biological Applications," Adv Mater. Mar. 5, 2010;22(9):920-32 (13 pages).

Kalfon-Cohen, Estelle et al., "Microstructure and nematic transition in thermotropic liquid crystalline fibers and their single polymer composites," Polym. Adv. Technol., 2007. 18(9): p. 771-779 (9 pages).
Kalejs, et al., "St. Jude Epic Heart Valve Bioprostheses Versus Native Human and Porcine Aortic Valves—Comparison of Mechanical Properties," Interactive Cardiovascular and Thoracic Surgery 8 (2009) 553-557 (5 pages).
Kang, Jungmee et al., "Polyisobutylene-Based Polyurethanes with Unprecedented Properties and How They Came About," Journal of Polymer Science Part A: Polymer Chemistry, 2011. 49(18): p. 3891-3904 (14 pages).
Khondker, O.A. et al., "Fabrication and mechanical properties of aramid/nylon plain knitted composites," Composites Part A: Applied Science and Manufacturing, 2004. 35(10): p. 1195-1205 (11 pages).
Kim, Nam K. et al., "Nanofibrillar Poly(vinylidene fluoride): Preparation and Functional Properties," Int. J. Polym. Mater. Polym. Biomater., 2014. 63(1): p. 23-32 (10 pages).
Kim, Nam K. et al., "Polymer-Polymer and Single Polymer Composites Involving Nanofibrillar Poly(vinylidene Fluoride): Manufacturing and Mechanical Properties," J. Macromol. Sci., Part B: Phys., 2014. 53(7): p. 1168-1181 (14 pages).
Kuang, Jinghao et al., "Universal Surface-initiated Polymerization of Antifouling Zwitterionic Brushes Using a Mussel Mimetic Peptide Initiator," Langmuir. May 8, 2012; 28(18): 7258-7266 (20 pages).
"Liquid-Crystal Polymer," Wikipedia, the Free Encyclopedia <http://en/wikipedia.org/wiki/Liquid-crystal_polymer>, retrieved Jun. 2, 2016 (3 pages).
Liu, et al., "Effect of fiber orientation on the stress distribution within a leaflet of a polymer composite heart valve in the closed position," J of Biomedichanics, 2007, 40:1099-1106 (8 pages).
Maity, J. et al., "Homocomposites of chopped fluorinated polyethylene fiber with low-density polyethylene matrix," Mater. Sci. Eng., A, 2008. A479(1-2): p. 125-135 (11 pages).
Masoumi, et al., "Trilayered Elastomeric Scaffolds for Engineering Heart Valve Leaflets," Biomaterials. Sep. 2014; 35(27):7774-7785 (28 pages).
Matabola, K. P. et al., "Single polymer composites: a review," Journal of Materials Science, 2009. 44(23): p. 6213-6222 (10 pages).
Medeiros Araujo, Thiago et al., "Liquid crystalline single-polymer short-fibers composites," Composite Interfaces, 2013. 20(4): p. 287-298 (12 pages).
Ohri, Rachit et al., "Hyaluronic acid grafting mitigates calcification of glutaraldehyde-fixed bovine pericardium," J Biomed Mater Res 70A: 328-334, 2004 (7 pages).
Schneider, Tobias et al., "Influence of fiber orientation in electrospun polymer scaffolds on viability, adhesion and differentiation of articular chondrocytes," Clinical Hemorheology and Microcirculation 52 (2012) 325-336 (13 pages).
"Second Office Action," for Chinese Patent Application No. 201380044842.0, dated Aug. 12, 2016 (16 pages) with summary.
Sun, Xiaoli et al., "α and β Interfacial Structures of the iPP/PET Matrix/Fiber Systems," Macromolecules, 2007. 40(23): p. 8244-8249 (6 pages).
Tu, Qin et al., "Synthesis of polyethylene glycol- and sulfobetaine-conjugated zwitterionic poly(l-lactide) and assay of its antifouling properties," Colloids and Surfaces B; Biointerfaces 102 (2013) 331-340 (10 pages).
Vesely, et al., "Micromechanics of the Fibrosa and the Ventricularis in Aortic Valve Leaflets," J Biomech. 1992 25(1):101-113 (12 pages).
Vick, Linda W. et al., "Hot compaction and consolidation of polycarbonate powder," Polym. Eng. Sci., 1998. 38(11): p. 1824-1837 (14 pages).
Wang, Qiang et al., "A novel small animal model for biocompatibility assessment of polymeric materials for use in prosthetic heart valves," J Biomed Mater Res 93A: 442-453, 2010 (12 pages).
Wang, Qiang et al., "In-Vivo Assessment of a Novel Polymer (SIBS) Trileaflet Heart Valve," J Heart Valve Dis, Jul. 2010, 19(4):499-505 (7 pages).
Ward, I.M. et al., "Developments in oriented polymers," Plastics, Rubber and Composites, 2004. 33(5): p. 189-194 (6 pages).

(56) References Cited

OTHER PUBLICATIONS

Ward, I.M. et al., "Novel composites by hot compaction of fibers," Polym. Eng. Sci., 1997. 37(11): p. 1809-1814 (6 pages).
Wheatley, et al., "Polyurethane: material for the next generation of heart valve prostheses?," Eur J Cardio-Thoracic Surg, 2000, 17:440-448 (11 pages).
Yang, Mingjing et al., "Assessing the Resistance to Calcification of Polyurethane Membranes Used in the Manufacture of Ventricles for a Totally Implantable Artificial Heart," J Biomed Mater Res (Appl Biomater) 48: 648-659, 1999 (12 pages).
Yao, Jian et al., "High Strength and High Modulus Electrospun Nanofibers," Fibers 2014; 2:158-187 (30 pages).
Yeh, Shiou-Bang et al., "Modification of Silicone Elastomer with Zwitterionic Silane for Durable Antifouling Properties," Langmuir 2014, 30, 11386-11393 (8 pages).
Zhang, Baoyan et al., "Studies of Novel Segmented Copolyether Polyurethanes," Eur. Polym. J., vol. 34, No. 3-4, pp. 571-575 (1998) (5 pages).
Zhang, Zhiping et al., "Effect of Crosslinking and Grafting by 60Co-γ-ray Irradiation on Carbon Black/Polyethylene Switching Materials and Fluoride Resin System in self-regulating Heating Cables," JAERI-Conf, 2000. 2000-001(JCBSRC '99, the 8th Japan-China Bilateral Symposium on Radiation Chemistry, 1999): p. 202-210 (9 pages).
Zhao, Zeng Hua et al., "Research development of single polymer composite preparation," Gongcheng Suliao Yingyong, 2010. 38(2): p. 81-84, with machine translation (11 pages).
"International Search Report and Written Opinion," for PCT application No. PCT/US2016/050691 dated Dec. 19, 2016 (14 pages).
"Non-Final Office Action," for U.S. Appl. No. 14/656,044 dated Mar. 17, 2017 (34 pages).
"Response to Communication Pursuant to Article 94(3) EPC," for European Patent Application No. 13739321.1 filed with the EPO Jan. 2, 2017 (37 pages).
"Response to Final Office Action," for U.S. Appl. No. 14/656,044, dated Sep. 9, 2016 and filed with the USPTO Dec. 8, 2016 (9 pages).
Berkland, Cory et al., "Controlling surface nano-structure using flow-limited field-injection electrostatic spraying (FFESS) of poly(D,L-lactide-co-glycolide)," Biomaterials (2004) 25: 5649-5658.
Fabreguette, et al., "X-ray mirrors on flexible polymer substrates fabricated by atomic layer deposition," Thin Solid Films 515: 7177-7180 (2007).
Fabreguette, Francois H. et al., "Ultrahigh x-ray reflectivity from W/Al2O3 multilayers fabricated using atomic layer deposition," Applied Physics Letters 88: 013166 (2006) 3 pages.
"Final Office Action," for U.S. Appl. No. 15/193,794 dated May 23, 2018 (12 pages).
George, "Final Report—Fabrication of Nanolaminates with Ultrathin Nanolayers Using Atomic Layer Deposition: Nucleation & Growth Issues," AFOSR Grant No. FA9550-01-1-0075 Feb. 2009 (36 pages).
Groner, M. D. et al., "Gas Diffusion Barriers on Polymers Using Al2O3 Atomic Layer Deposition," Applied Physics Letters 88, 051907, 2006 (3 pages).
Hass, D. D. et al., "Reactive vapor deposition of metal oxide coatings," Surface and Coatings Technology 146-147 (2001) 85-93.
"International Preliminary Report on Patentability," for PCT Application No. PCT/US2016/050691 dated Mar. 29, 2018 (9 pages).
"International Search Report and Written Opinion," for PCT Application No. PCT/US2017/032656 dated Jul. 21, 2017 (16 pages).
Jen, Shih-Hui et al., "Critical tensile and compressive strains for cracking of Al2O3 films grown by atomic layer deposition," Journal of Applied Physics 109, 084305 (2011), 11 pages.
Jen, Shih-Hui et al., "Critical tensile strain and water vapor transmission rate for nanolaminate films grown using Al2o3 atomic layer deposition and alucone molecular layer deposition," Applied Physics Letters 101, 234103 (2012), 3 pages.
Mach, H. et al., "Highly Reactive Polyisobutene as a Component of a New Generation of Lubricant and Fuel Additives," Lubrication Science 1999, 11 (2), 175-185.
"Non-Final Office Action," for U.S. Appl. No. 15/082,239 dated May 16, 2018 (34 pages).
"Notification of Patent Reexamination," for Chinese Patent Application No. 201380044842.0 dated Feb. 7, 2018 (12 pages) with English summary.
Raghavan, R. et al., "Nanocrystalline-to-amorphous transition in nanolaminates grown by low temperature atomic layer deposition and related mechanical properties," Applied Physics Letters 100, 191912 (2012), 9 pages.
"Response to Communication Pursuant to Rules 161(1) and 162 EPC," for European Patent Application No. 16715218.0 filed May 25, 2018, 13 pages.
"Response to Communication Pursuant to Rules 161(1) and 162 EPC," for European Patent Application No. 16715724.7 filed May 25, 2018, (7 pages).
"Response to Non-Final Office Action," for U.S. Appl. No. 15/193,794, dated Mar. 14, 2018 and filed with the USPTO Apr. 16, 2018 (8 pages).
Rutledge, G.C. et al., "Electrostatic Spinning and Properties of Ultrafine Fibers," National Textile Center Annual Report: Nov. 2001, M01-D22, (10 pages).
Shin, Y. M. et al., "Experimental characterization of electrospinning: the electrically forced jet and instabilities," Polymer 42 (2001) 9955-9967.
Szeghalmi, Adriana et al., "All dielectric hard x-ray mirror by atomic layer deposition," Applied Physics Letters 94, 133111 (2009), 3 pages.
Szilagyi, Imre M. et al., "Review on One-Dimensional Nanostructures Prepared by Electrospinning and Atomic Layer Deposition," INERA Workshop of ISCMP2014, IOP Publishing, Journal of Physics: Conference Series 559, 2014 (13 pages).

* cited by examiner

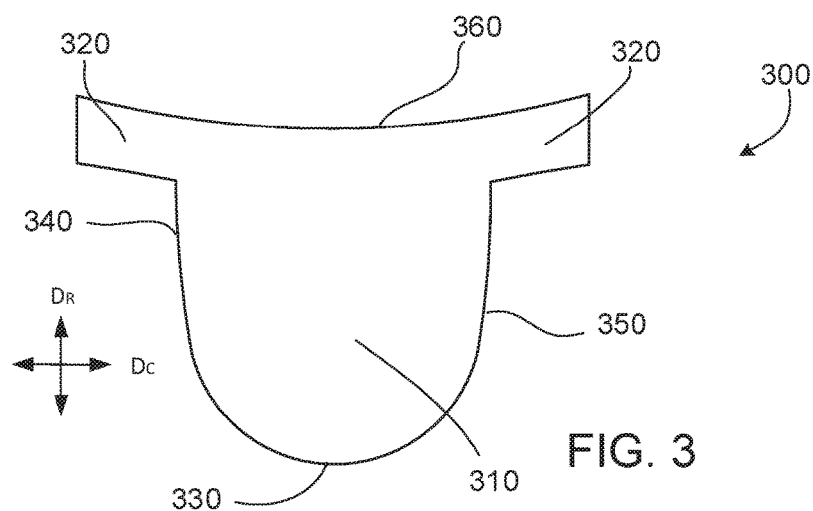
FIG. 3
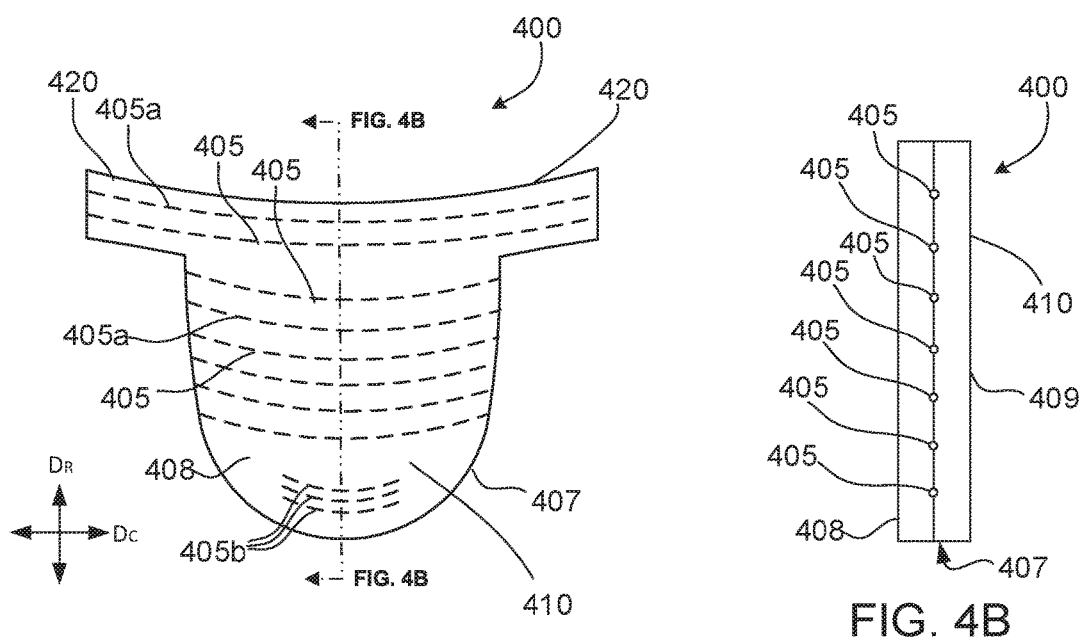
FIG. 4A
FIG. 4B

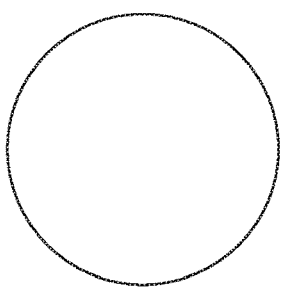
FIG. 7
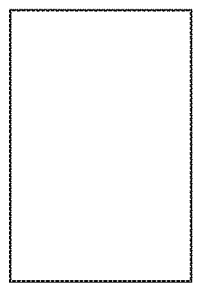
FIG. 8
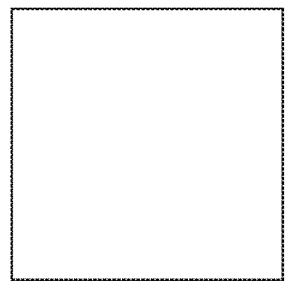
FIG. 9
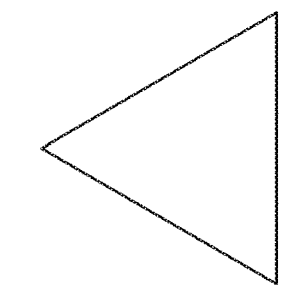
FIG. 10
FIG. 11
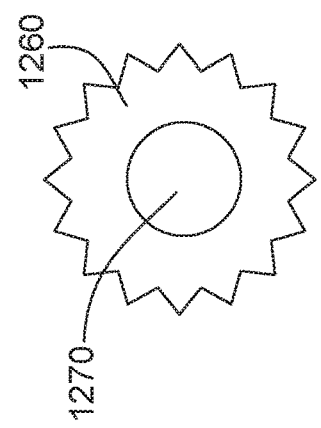
FIG. 12
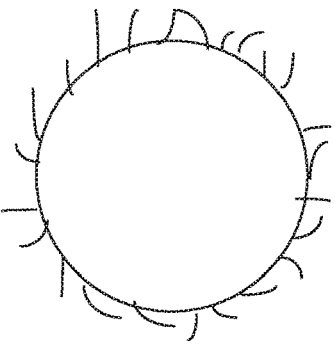
FIG. 13

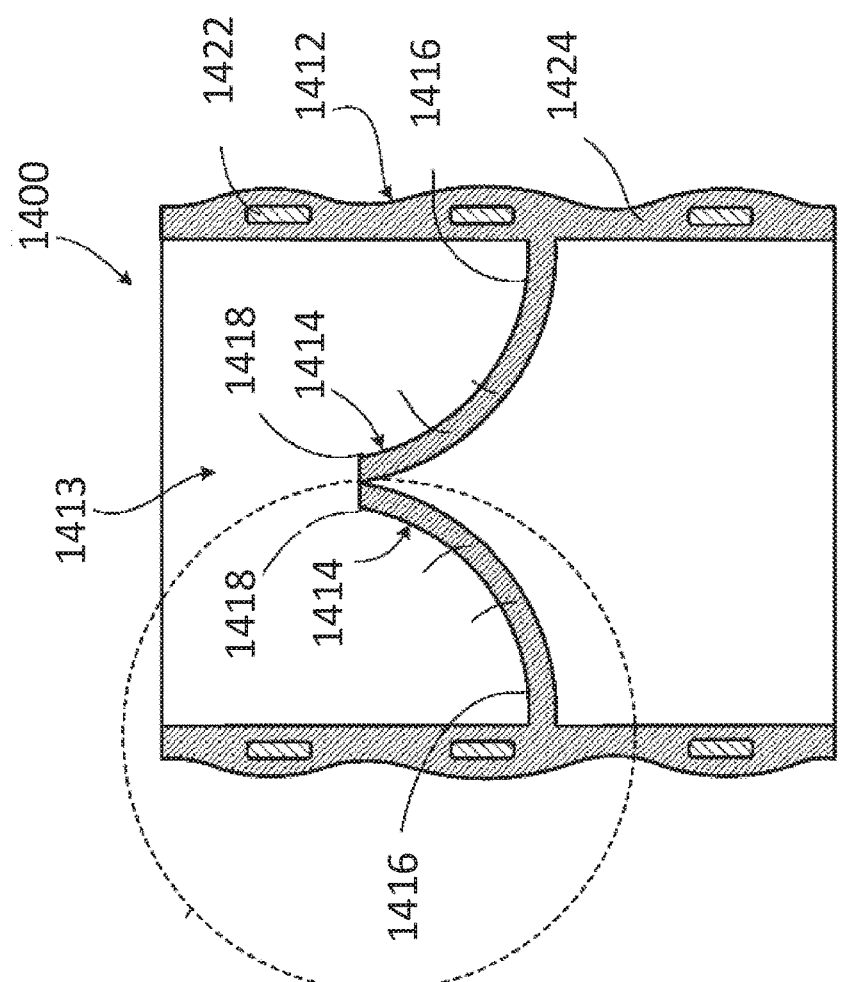

PROSTHETIC HEART VALVES INCLUDING PRE-STRESSED FIBERS

This application claims the benefit of U.S. Provisional Application No. 62/218,776, filed Sep. 15, 2015, the contents of which are herein incorporated by reference.

TECHNICAL FIELD

The present invention relates to prosthetic heart valves that include pre-stressed fibers and methods related thereto.

BACKGROUND

More than 250,000 heart valves are replaced worldwide each year due to structural defects, such as valve stenosis, which may lead to regurgitation. Valve stenosis is a condition where a heart valve is not able to fully open when blood is pumped through the heart due to heart valve leaflets becoming too stiff, or partially fused together. Valve stenosis creates a narrowed opening that stresses the heart, which in turn can cause fatigue and/or dizziness in a patient. Regurgitation, the backward flow of blood in the heart, can reduce blood pumping efficiency of the heart such that a patient experiences fatigue or a shortness of breath.

Long term implants, such as prosthetic heart valves, can be used to replace a diseased heart valve. Some prosthetic heart valves are made entirely of synthetic materials, while others are made of a combination of synthetic materials and animal tissues, for example, bovine or porcine pericardium. Prosthetic heart valves made of synthetic materials can have inadequate long term chemical stability and/or cause undesirable biological responses in a patient. Alternatively, prosthetic heart valves made of animal tissues are often vulnerable to structural deterioration caused by calcification, causing the narrowing of the valve orifice, or cusp tearing. There is a need for a prosthetic heart valve with long term chemical stability and mechanical properties that can mimic a native heart valve.

SUMMARY

Disclosed herein are various embodiments of prosthetic heart valves that include pre-stressed reinforcement elements, such as pre-stressed fibers, and methods related thereto.

In Example 1, a prosthetic heart valve includes a base and one or more heart valve leaflets. At least a portion of the leaflet can include a composite material that contains a polymer substrate and a pre-stressed reinforcement element at least partially disposed in the polymer substrate.

In Example 2, the prosthetic heart valve of Example 1, wherein the pre-stressed reinforcement element is bonded to the polymer substrate at two or more discrete locations along a length of the pre-stressed reinforcement element.

In Example 3, the prosthetic heart valve of Example 1 or Example 2, wherein the polymer substrate and the pre-stressed reinforcement elements include different materials. For instance, the polymer substrate can include a first material and the pre-stressed reinforcement elements can include a second material, in which the first material is a different material than the second material.

In Example 4, the prosthetic heart valve of one of Examples 1-3, wherein the polymer substrate includes at least two polymer layers and the pre-stressed reinforcement element is disposed between the at least two polymer layers.

In Example 5, the prosthetic heart valve of one of Examples 1-4, wherein the pre-stressed reinforcement element includes a metal.

In Example 6, the prosthetic heart valve of Example 5, wherein the pre-stressed reinforcement element includes nitinol.

In Example 7, the prosthetic heart valve of one of Examples 1-6, wherein the pre-stressed reinforcement element includes a polymer.

In Example 8, the prosthetic heart valve of Example 7, wherein the pre-stressed reinforcement element includes polyetheretherketone (PEEK) or polyethersulfone (PES).

In Example 9, the prosthetic heart valve of one of Examples 1-8, wherein the polymer substrate includes polyisobutylene polyurethane (PIB-PUR).

In Example 10, the prosthetic heart valve of one of Examples 1-9, wherein the pre-stressed reinforcement element is configured to be in tension when the polymer substrate is in a non-strained state.

In Example 11, the prosthetic heart valve of one of Example 1-10, wherein the pre-stressed reinforcement element is in tension, at least a portion of the polymer substrate is in compression, or both.

In Example 12, the prosthetic heart valve of one of Examples 1-11, wherein the pre-stressed reinforcement element includes a plurality of fibers.

In Example 13, the prosthetic heart valve of one of Examples 1-12, wherein the pre-stressed reinforcement element includes a mesh.

In Example 14, a method of manufacturing a prosthetic heart valve leaflet includes disposing a plurality of fibers between first and second polymeric layers. The method also includes applying a predetermined axial force to the plurality of fibers and coupling the plurality of fibers to the first and second layers. The method includes applying the predetermined axial force to the plurality of fibers during the coupling step.

In Example 15, the method of Example 14, wherein the applying predetermined axial force includes applying a tensile force to the plurality of fibers.

In Example 16, the method of Example 14 or Example 15, wherein the applying axial force includes applying a tensile force ranging from about 0.5 pound-force 2.22 newtons) to about 1 pound-force (4.45 newtons).

In Example 17, the method of one of Examples 14-16, wherein the applying of the predetermined axial force to the plurality of fibers comprises elastically deforming the reinforcement fiber to a predetermined elongation percentage while the first and second layers are being coupled to the plurality of fibers.

In Example 18, the method of one of Examples 14-17, wherein the coupling step includes compression molding or dip coating the first and second layers to the plurality of fibers.

In Example 19, the method of one of Examples 14-18, wherein disposing the plurality of fibers includes aligning the plurality of fibers in a circumferential direction of the heart leaflet, a radial direction of the heart leaflet, or both.

In Example 20, especially the prosthetic heart valve of one of Examples 1-12, a prosthetic heart valve includes a base and one or more heart valve leaflets. Each leaflet can include a body in which at least a portion of the body includes a composite material containing a polymer substrate and a pre-stressed mesh embedded within the polymer substrate. At least a portion of the pre-stressed mesh can be embedded within the polymer substrate such that the pre-stressed mesh is tensioned in a first direction along the body of the leaflet. The body of a leaflet can be the entire leaflet or select portions of the leaflet, for example, a central portion (e.g., body portion) of the body that does not include sleeve portions.

In Example 21, a prosthetic heart valve includes a base and two heart valve leaflets. Each leaflet is characterized by at least a portion of the leaflet that has a composite material that includes a polymer substrate and a pre-stressed reinforcement element disposed within the polymer substrate.

In Example 22, the prosthetic heart valve of Example 21, wherein the pre-stressed reinforcement element is a composite that includes a metal and a polymer.

Some or all of the prosthetic heart valves, leaflets, and methods provided herein may provide one or more of the following advantages. In some cases, the prosthetic heart valve provided herein includes a heart valve component, e.g., a heart valve leaflet, composed of one or more synthetic composite materials having elastic properties that are similar to native heart tissue. In particular, heart valve leaflets provided herein can be composed of pre-stressed reinforcement elements (e.g., fibers) that allow the leaflet to repeatedly elongate with a spring-like tension. In some cases, the pre-stressed fibers within prosthetic heart valve leaflets can be similar to, or emulate, properties exhibited by collagen fibers by providing the leaflet with anisotropic properties. In some cases, the pre-stressed fibers can create a curved, accordion, or folded configuration in the leaflet material when the leaflet is in a relaxed (non-stressed) state, and a straight pattern when the leaflet is in an active (stressed) state. In some cases, prosthetic heart valves provided herein include composite materials containing pre-stressed fibers that have increased durability as compared to composite materials that do not contain pre-stressed fibers. For example, prosthetic heart valve leaflets composed of pre-stressed fibers may help lower stresses to the leaflet as a whole during systole and diastole because the pre-stressed fibers can provide the leaflet with an initial tensile load that reduces the likelihood of the leaflet material over-stretching during muscular contractions associated with systole or diastole. In some cases, the prosthetic heart valve provided herein can provide a heart valve material having a higher or lower elongation as compared to composite materials that do not have pre-stressed fibers.

BRIEF DESCRIPTION OF THE DRAWINGS

FIG. 3 is a plan view of an exemplary leaflet provided herein.

FIGS. 4A and 4B are a plan view and a side view, respectively, of an exemplary leaflet provided herein.

FIGS. 7-13 are cross-sectional views of a pre-stressed reinforcement element (e.g., fiber) in accordance with various embodiments described herein.

FIG. 14 is an illustration of another exemplary prosthetic heart valve provided herein.

DETAILED DESCRIPTION

Figure 1:
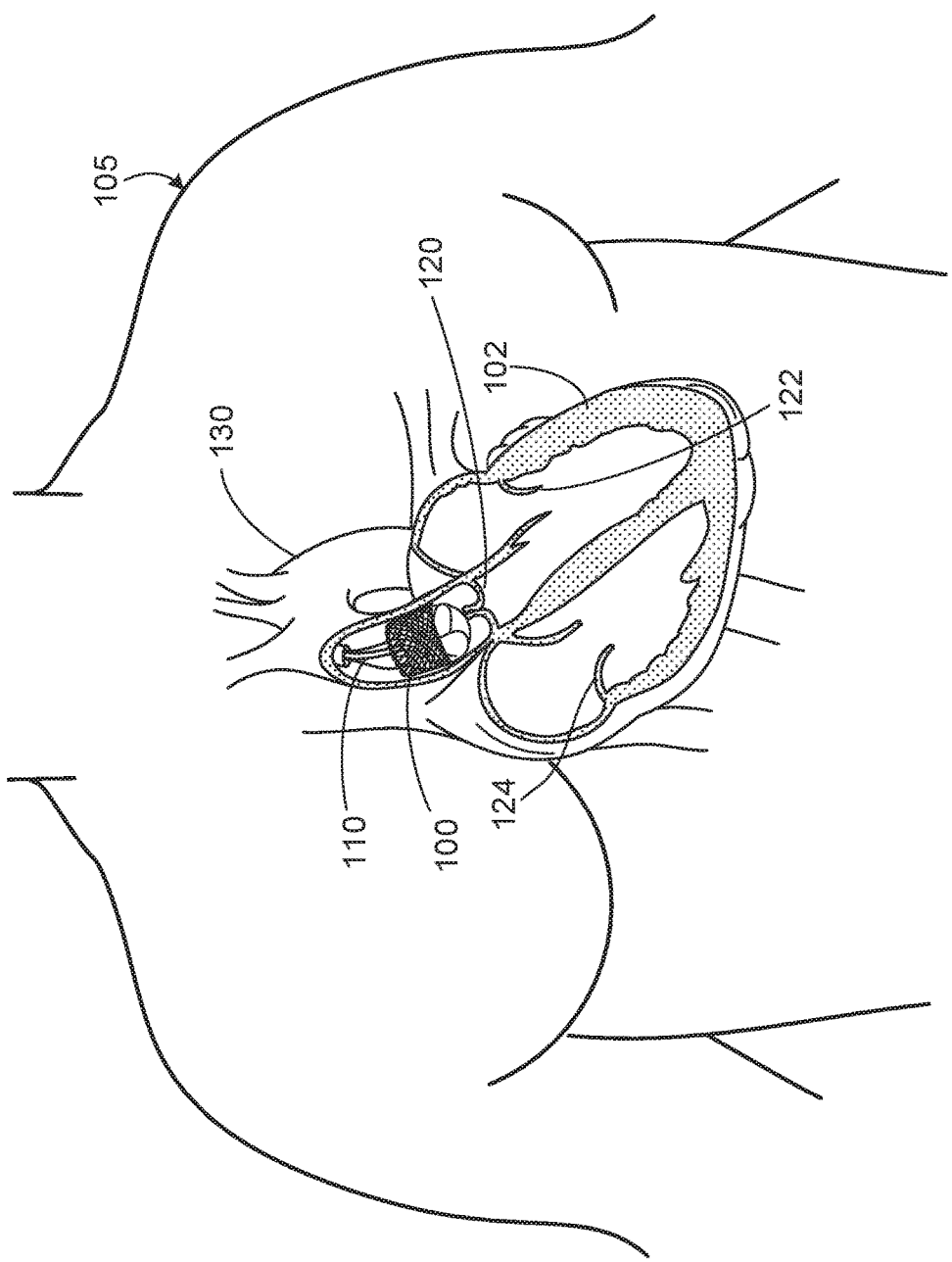
FIG. 1 is an illustration of an exemplary prosthetic heart valve provided herein within a human anatomy.

FIG. 1 shows an illustration of a prosthetic heart valve 100 provided herein within a heart 102 of a human body 105. The human body 105 has four heart valves: a pulmonary valve, a tricuspid valve, an aortic valve 120 and a mitral valve. The purpose of the heart valves is to allow blood to flow through the heart and from the heart into the major blood vessels connected to the heart, such as the aorta 130 and pulmonary artery. Prosthetic heart valve 100 of FIG. 1 is an aortic prosthetic heart valve that can be delivered using a transcatheter aortic valve replacement (TAVR) procedure (which can be described as percutaneous aortic valve replacement (PAVR) or transcatheter aortic valve implantation (TAVI)) involving the use of a deployment device 110 (e.g., a delivery catheter) placed through blood vessels from a femoral, subclavian, or direct aortic incision (not shown). Deployment device 110 can deliver prosthetic heart valve 100 to a desired location within the anatomy, and release implantable heart valve 100 at an implantation site. Although FIG. 1 shows an aortic prosthetic heart valve 100, it should be appreciated by one skilled in the art that prosthetic heart valve 100 provided herein can include other types of heart valves (e.g., a mitral valve 122 or a tricuspid valve 124), in some cases. In some cases, the prosthetic heart valve provided herein may be applicable to other types of valves within the body, such as valves within a peripheral vein for preventing blood regurgitation. In some cases, the prosthetic heart valve provided herein may be delivered using a transcatheter valve replacement deployment device (e.g., a delivery catheter).

Figure 2:
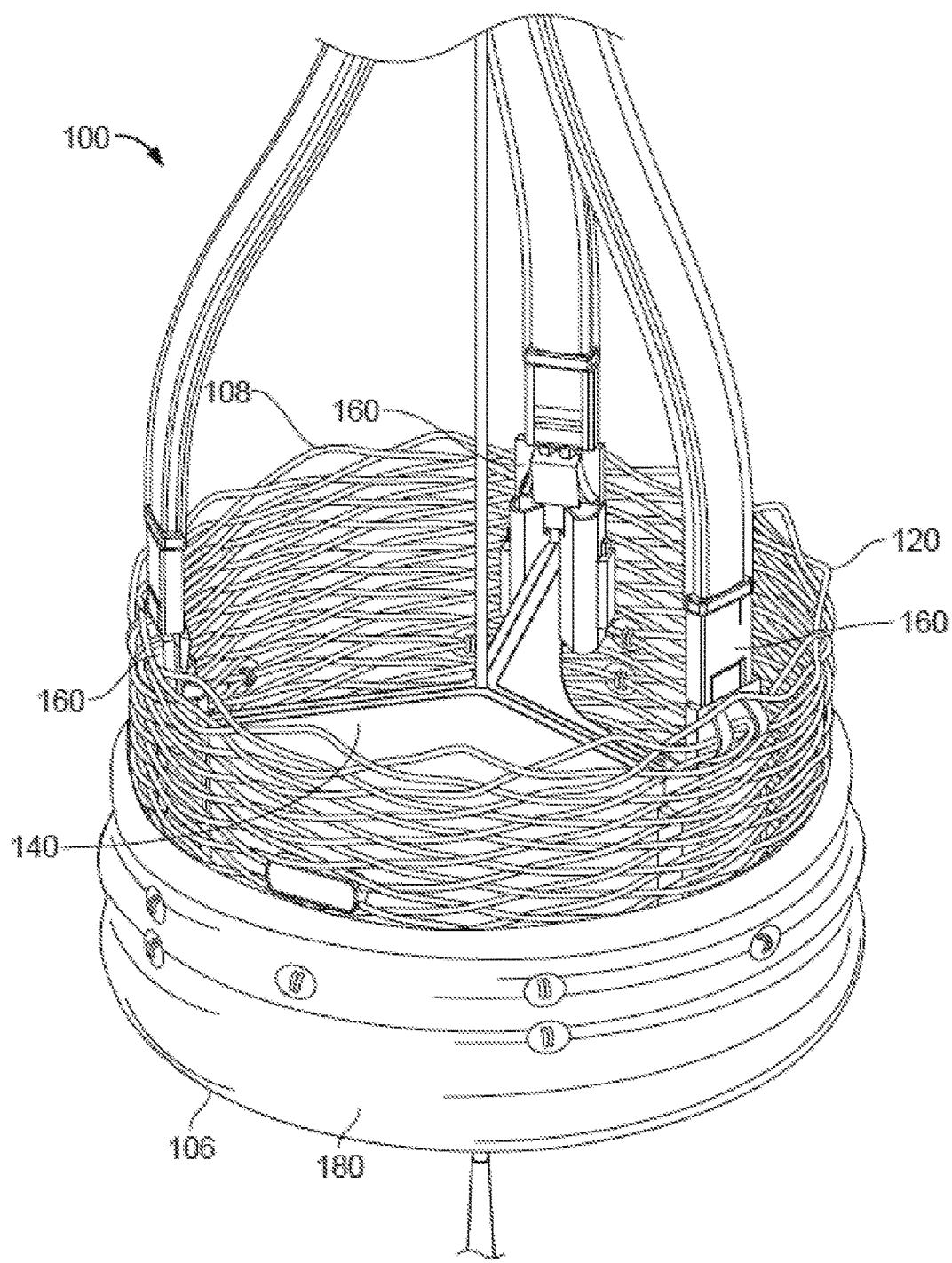
FIG. 2 is an enlarged view of the prosthetic heart valve of FIG. 1.

FIG. 2 provides a close up view of the prosthetic heart valve 100 of FIG. 1. The depicted embodiment of prosthetic valve 100 includes an inflow end 106 and an outlet end 108. Prosthetic heart valve 100, as shown in FIG. 2, has a substantially tubular body 120, a plurality of leaflets 140, anchor elements 160, and a tubular seal 180. Tubular body 120 can be a radially expandable member (e.g. annular frame or stent) that includes an annular cavity. As shown in FIG. 2, the heart valve 100 can have three heart valve leaflets 140 coupled to the tubular body 120 within the annular cavity. Three anchor elements 160 positioned within the annular cavity of the tubular body 120 can each secure the heart valve leaflets to the tubular body 120. Each anchor element 160, in some cases, can be anchored to the tubular body 120 and clamped to the leaflets. The tubular seal 180 can be disposed about at least a portion of the tubular body 120, in some cases. In particular, in some cases, the tubular seal can have an inflow end portion secured to bottom edges of the plurality of leaflets at the inflow end 106 and have an outflow end portion disposed about an outer surface of the tubular body 120 at the outflow end 108 to restrict blood flow around the leaflets.

Prosthetic heart valve 100 can include various materials. In some cases, at least a portion of the prosthetic heart valve 100, for example, the leaflets 140 or a portion of the tubular body 120, can contain various synthetic materials. In some cases, the prosthetic heart valve 100 can be made entirely of synthetic materials. The synthetic materials of the prosthetic heart valve 100 can include polymeric materials, metals, ceramics, and combinations thereof. In some cases, synthetic materials of the prosthetic heart valve 100 can include composite structures. In some cases, as will be discussed in further sections, a prosthetic heart valve can include materials containing pre-stressed reinforcement elements, such as pre-stressed fibers.

In use, prosthetic heart valve 100 can be implanted surgically or delivered by transcatheter delivery into a mammalian heart. As the heart valve closes, edge portions of the polymeric leaflets 140 can move into coaptation with one another to substantially restrict fluid from flowing past prosthetic heart valve 100. As the heart valve is opening, the edge portions of the leaflets 140 can move away from one another, permitting fluid to flow past prosthetic heart valve 100. Movement of the leaflets between the closed and open positions can substantially approximate the hemodynamic performance of a healthy natural valve.

FIG. 3 shows an example of a prosthetic heart valve leaflet 300 provided herein. As shown, leaflet 300 can include a body portion 310 (or belly region of the leaflet) and two sleeve portions 320 that extend outwardly from the body portion 310. In some cases, the body portion 310 has a bottom edge 330, a first side edge 340, a second side edge 350, and a free edge 360. Leaflet 300 further includes a front side (i.e., the side that blood flows toward) and a back side (i.e., the side that blood flows away from). The bottom edge 330 and side edges 340, 350 of the body portion 310 can be shaped for suturing and for forming a leaflet profile similar to a native valve. The sleeve portions 320 can be shaped to be compatible with anchor elements, such as anchor elements 160 of FIG. 2.

As the prosthetic heart valve opens and closes, each leaflet flexes between the open position and the closed position. As the heart pulsates, the leaflet 300 can elongate in various directions as the valve opens and closes, thus tensile and flexural strains on each leaflet may change depending on the leaflet's position. For instance, the leaflet 300 can elongate along the body portion 310 and/or the sleeve portions 320, as shown by the arrows in FIG. 3, in a radial direction $D_R$, or a circumferential direction $D_C$, or both. The radial direction $D_R$ of a leaflet in a heart valve can include a radially inward direction or a radially outward direction. As shown in FIG. 3, the radial direction $D_R$ extends from the free edge 360 to the bottom edge 330 of the leaflet. The circumferential direction $D_C$ extends circumferentially along a heart valve, e.g., an inner circumference of the tubular body 120 of FIG. 2. As shown in FIG. 3, the circumferential direction $D_C$ on the depicted leaflet 300 generally extends from one side edge to the opposite side edge of the sleeve portion. In some cases, the circumferential direction $D_C$ can generally extend in a direction generally orthogonal to the radial direction $D_R$. The circumferential direction $D_C$ can also extend from one side of the body portion (e.g., the first side edge 340) to an opposite side of the body portion (e.g., the second side edge 350), which can be described as a circumferential direction $D_C$ in the belly region of the leaflet 300. In some cases, the leaflet 300 can elongate in an oblique direction relative to the radial and circumferential directions. Due to the various directions of elongation that a prosthetic leaflet can experience during use, the heart leaflet provided herein can greatly benefit from containing materials having anisotropic physical and mechanical properties, for example, materials containing pre-stressed reinforcement elements described herein.

Prosthetic heart valves provided herein, in some cases, can include a base and one or more heart valve leaflets, in which least a portion of each leaflet includes a composite material. In particular, in some cases, leaflets provided herein can contain a composite material that includes a pre-tensioned (or tensionally pre-stressed) reinforcement element to provide the heart leaflet with anisotropic properties. Alternatively, in some cases, the leaflets may include a pre-compressed (or compressionally pre-stressed) reinforcement element. The term "pre-stressed" in this document describes both pre-tensioned and pre-compressed reinforcement elements.

The composite material of the prosthetic heart valve leaflets provided herein can also include a polymer substrate, e.g., one or more polymer layers, that surrounds (or encapsulates) the pre-stressed reinforcement element. The pre-stressed reinforcement element can help increase the durability of heart valve leaflet by producing a compressive stress that balances the tensile stress that the polymer substrate would otherwise experience during use. In various cases, the composite material can include polymer layers containing a different material than the pre-stressed reinforcement element to provide the leaflet provided herein with the desired mechanical properties. For example, the pre-stressed reinforcement element can include a first material, such as nitinol, and the polymer layers can include a second material, such as polyurethane. In some cases, the pre-stressed reinforcement element can be a pre-stressed fiber or a pre-stressed wire. In some cases, the heart valves provided herein include at least one leaflet that includes a plurality of fibers (or wires). The prosthetic heart valve provided herein can include other components, such as the base, that contain a composite structure that includes one or more pre-stressed reinforcement elements.

FIGS. 4A and 4B show an example of a prosthetic heart valve leaflet 400 provided herein that includes a composite material with circumferentially aligned reinforcement elements 405 (e.g., pre-stressed fibers), which are depicted by the dotted lines in FIG. 4A, embedded within polymeric substrate 407 (e.g., one or more polymer layers). In some cases, as best shown in FIG. 4B, the polymer substrate 407 can include at least two polymeric layers, a first polymeric layer 408 and a second polymeric layer 409. The depicted leaflet 400 includes a plurality of pre-stressed reinforcement elements 405 that extend in a circumferential direction $D_C$ across a body portion 410 and two sleeve portions 420. In some cases, the leaflet 400 can optionally include at least one reinforcement element 405a along the entire circumferential (or radial) length of the leaflet 400. In some cases, the pre-stressed reinforcement elements 405b can extend along a portion of the leaflet (e.g., partially extending along the circumferential length of the leaflet).

In some cases, a prosthetic heart valve leaflet 400 provided herein can include of a plurality of pre-stressed reinforcement elements 405 (e.g., fibers) in which a portion of the pre-stressed reinforcement elements 405 are pre-tensioned or pre-compressed. For example, pre-stressed reinforcement elements 405 of the leaflet 400 extending along a circumferential direction $D_C$ may be pre-stressed, but the pre-stressed reinforcement elements 405 extending along a radial distance $D_R$ may not be pre-stressed in some cases. For example, pre-stressed reinforcement elements 405 may be tensioned or compressed in the direction of one axis only or the pre-stressed reinforcement elements 405 may be tensioned or compressed in the direction of two axes, e.g. along a circumferential direction and along a radial direction.

The polymer substrate 407, e.g., one or more polymer layers, of the prosthetic heart valves provided herein can partially or fully encapsulate or surround the pre-stressed reinforcement elements. Accordingly, in some cases, the prosthetic heart valve leaflets 400 provided herein can include a composite material containing a plurality of reinforcement elements 405 (e.g., fibers) that are fully embedded in the polymer substrate 407. Alternatively, in some cases, the pre-stressed reinforcement elements 405 can be embedded within a portion of the polymer substrate 407. In some cases, a prosthetic heart valve leaflet can include pre-stressed reinforcement elements 405 at least partially exposed on the surface of the polymer substrate 407, or at least one of the polymer layers 408, 409.

The pre-stressed reinforcement element 405 may be bonded to the polymeric substrate 407 by a chemical bond, a mechanical bond, or both. In some cases, the pre-stressed reinforcement element 405 can be bonded to the polymeric substrate 407 along the entire length of the pre-stressed reinforcement element 405. In some cases, the pre-stressed reinforcement element 405 can be bonded to the polymeric substrate 407 at two or more discrete locations along a length of the pre-stressed reinforcement element 405. For example, the pre-stressed reinforcement elements 405 can be bonded along peripheral edges of the leaflet 400 at the body portion 410 and/or the two sleeve portions 420.

Prosthetic heart valve leaflets 400 provided herein can include one or more pre-stressed reinforcement elements 405 that are tensioned, or relaxed, in relation to the surrounding polymer layers. For example, in some cases, a leaflet 400 at systole (or alternatively, at diastole) can include pre-stressed reinforcement elements 405 (e.g., pre-tensioned reinforcement elements) that are in tension (strained) while the surrounding polymer layers 407 are in an undeformed state (non-strained state). In some cases, a leaflet 400 at systole (or, alternatively, at diastole) can include one or more pre-tensioned reinforcement elements 405 in an undeformed (non-strained) state while the surrounding polymeric material 407 is in a compressed (strained) state. In some cases, the pre-tensioned reinforcement element can be in tension, at least a portion of the polymeric substrate can be in compression, or both. The pre-tensioned reinforcement elements 405 can help to reinforce the polymer layers 407 against fatigue-related failure by placing the polymer layers 407 in compression while the leaflet 400 is in a resting (e.g., non-stressed) state such that the tensile load and strain on the polymer layers 407 are minimized while the leaflet is in an active (e.g., stressed) state. Accordingly, the pre-tensioned reinforcement element can help increase the durability of heart valve leaflet by producing a compressive stress that balances the tensile stress that the polymer substrate would otherwise experience during device use.

Prosthetic heart valves leaflets provided herein (e.g., leaflet 400) can contain various medically suitable materials. In various cases, the heart valve leaflets provided herein can include a polymer substrate (e.g., polymer substrate 407) and/or reinforcement elements (e.g., elements 408, 409) containing a medically suitable polymeric material. Some exemplary polymeric materials can include, but are not limited to, polypropylenes, polyesters, polytetrafluoroethylenes (PTFE), polyethylenes, polyurethanes, polyetheretherketones (PEEK), polysulfones (PES), polycarbonates, polyethers, polyesters, polyamides, nylons, polyetherimides, and combinations thereof. Suitable polymers can include, but are not limited to, homopolymers, copolymers, and terpolymers. In some cases, the leaflets provided herein can be formed from block polymers such as, for example, poly(styrene-isobutylene-styrene) (SIBS) tri-block polymers. In some cases, the leaflets provided herein can contain elastomeric materials that include, but are not limited to, silicones, nitrile rubber, fluoroelastomers, polyolefin elastomers, latex-type elastomers, various natural elastomers such as those made from collagen, elastin, cellulose, proteins, carbohydrates and combinations thereof.

Various polyurethanes can be used, in some cases, to construct the pre-stressed reinforcement elements and/or the polymer layers of the prosthetic heart valves leaflets provided herein. In some cases, suitable polymers for forming a leaflet 400 provided herein can be made from polyurethanes, for example, polyisobutylene urethanes (PIB-PUR), polyurethane elastomers (e.g. Pellethane), polyether-based polyurethanes (e.g. Tecothane), polycarbonate-based polyurethanes (e.g. Bionate and/or Chronoflex) and combinations thereof. In some cases, exemplary polyurethanes include, but are not limited to, polyurethanes with soft segments such as polyether, perfluoropolyether, polycarbonate, polyisobutylene, polysiloxane, or combinations thereof. Polyurethane hard segments can include, but are not limited to, methylene diphenyl diisocyanate (MDI), 4,4'-Methylene dicyclohexyl diisocyanate and hexamethylene.

The pre-stressed reinforcement elements (e.g., fibers) of the prosthetic heart valves leaflets provided herein (e.g., elements 405 of leaflet 400) can contain various biocompatible materials, such as polymers, ceramics, metals, or combinations thereof. For example, the pre-stressed reinforcement elements can contain metals including, but not limited to, stainless steel, tantalum, carbon, titanium, nitinol, and combinations thereof. In some cases, pre-stressed reinforcement elements can contain one or more polymers provided herein. Pre-stressed reinforcement elements can, in some cases, include a plurality of pre-stressed electrospun polymer fibers. In some cases, the pre-stressed reinforcement elements can include a pre-stressed mesh composed of a plurality of fibers, which will be discussed later in greater detail with FIGS. 5 and 6.

In some cases, the prosthetic heart valves leaflets (e.g., leaflet 400 of FIG. 4) provided herein include one or more pre-stressed reinforcement elements (e.g., elements 405) containing a composite fiber that includes at least one metal and at least one polymer. For example, a pre-stressed reinforcement element may contain a polymer that includes metal particles embedded therein, in some cases. Another example may include, in some cases, a pre-stressed reinforcement element that includes a fiber that has a polymeric outer substrate disposed over one or more metal fibers (e.g., polymeric outer substrate 1260 disposed over a metal fiber 1270 in FIG. 12).

In some cases, the pre-stressed reinforcement elements (e.g., fibers) within a composite material of the leaflet provided herein (e.g., leaflet 400 of FIG. 4) can contain a liquid crystalline polymer (LCP). LCPs are a special class of aromatic polyesters or polyamide copolymers that have semi-crystalline properties due to regions of highly ordered crystalline structures formed therein. Suitable fiber materials containing LCPs can include, but are not limited to, thermotropic polyester such as Vectran®, poly(p-phenylene terephthalamide) (PPTA), and poly(phenylene benzobisoxazole) (PBO) and combinations thereof. Suitable LCPs can include Kevlar®, Vectran®, Nomex®, Herachron®, Technora®, Twaron®, and Zylon®. In some cases, high performance fibers can be utilized in composite materials, such as gel-spun ultra-high molecular weight polyethylene (Dyneema®). LCPs can provide the leaflets provided herein with pre-stressed reinforcement elements that have a high creep resistance, a high modulus, and a high tensile strength. LCPs may be used to form heart valve leaflets provided herein that have thinner and smaller dimensions, but sufficient strength, robustness, and durability to allow for proper heart valve function. In some cases, the diameter of LCP fibers can be as small as 0.5 micrometers (microns), or about 0.00002 inches. In some cases, the thickness of the leaflets provided herein that include LCP fibers can range from about 0.002 to about 0.004 inches (or about 50 microns to about 100 microns).

In some cases, pre-stressed reinforcement elements 405 (e.g., fibers) of the prosthetic heart valve leaflet provided herein (e.g., leaflet 400) can be composed of one or more materials. For example, leaflets provided herein can include a plurality of fibers in which a portion of the fibers contain a polyurethane while another portion of fibers contain a polyisobutylene polyurethane (PIB-PUR). Using pre-stressed reinforcement elements containing different materials in different areas of the leaflet can allow desired mechanical properties to be tailored, as desired, to appropriate locations of the heart leaflet.

In some cases, heart valve leaflets provided herein (e.g., leaflet 400) can include a pre-tensioned reinforcement element that is axially loaded to a predetermined percent elongation. For example, in some cases, pre-tensioned reinforcement elements (e.g, fibers) can be subjected to a tensile strain corresponding to a percent elongate ranging from about 1% to about 99%, or from about 25% to about 75%, including all values and ranges therebetween. Pre-tensioned reinforcement elements can subjected to a percent elongation, in some cases, ranging from about 1% to about 5%, from about 5% to about 10%, from about 10% to about 20%, from about 20% to about 30%, from about 30% to about 40%, from about 40% to about 50%, from about 50% to about 60%, from about 60% to about 70%, from about 70% to about 80%, from about 80% to about 100%, from about 100% to about 150%, from about 150% to about 200%, from about 200% to about 300%, or from about 300% to about 500%. In some cases, pre-tensioned reinforcement elements can be under a strain load corresponding to a percent elongation of at least 1%, at least 5%, at least 10%, at least 20%, at least 30%, at least 40%, at least 50%, at least 60%, at least 70%, at least 80%, at least 90%, at least 100%, at least 150%, at least 200%, at least 300%, at least 400%, or at least 500%. In some cases, pre-tensioned reinforcement elements can be subjected to a percent elongation of more than about 1%, about 5%, about 10%, about 20%, about 30%, about 40%, about 50%, about 60%, about 70%, about 80%, about 90%, about 100%, about 150%, about 200%, about 300%, about 400%, 500%, or more than about 500%.

Figure 5:
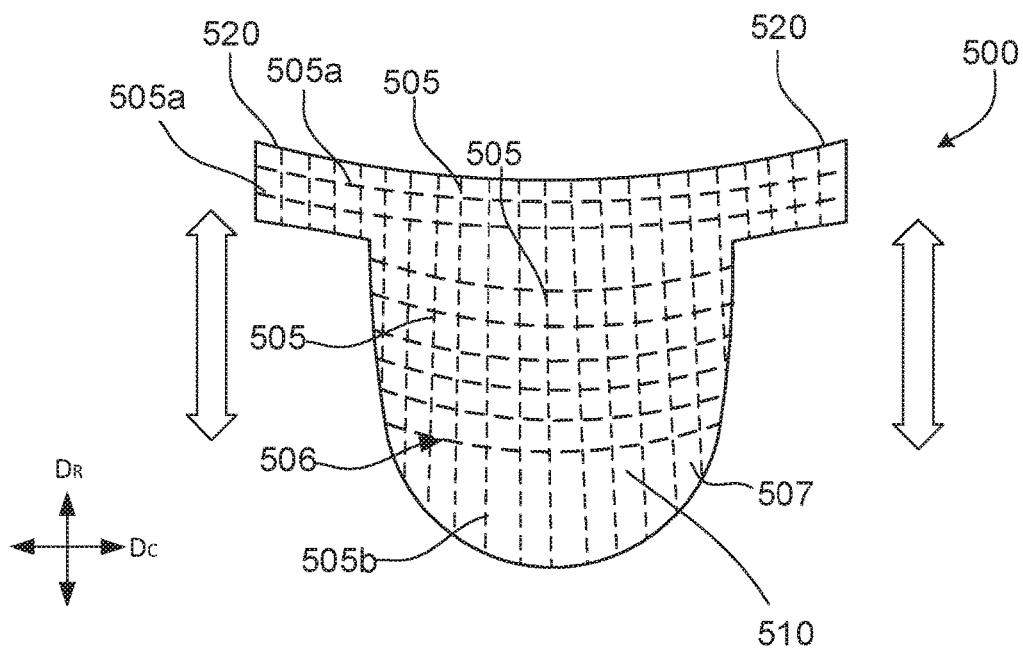
FIGS. 5 and 6 are plan views of exemplary leaflets provided herein.
Figure 6:
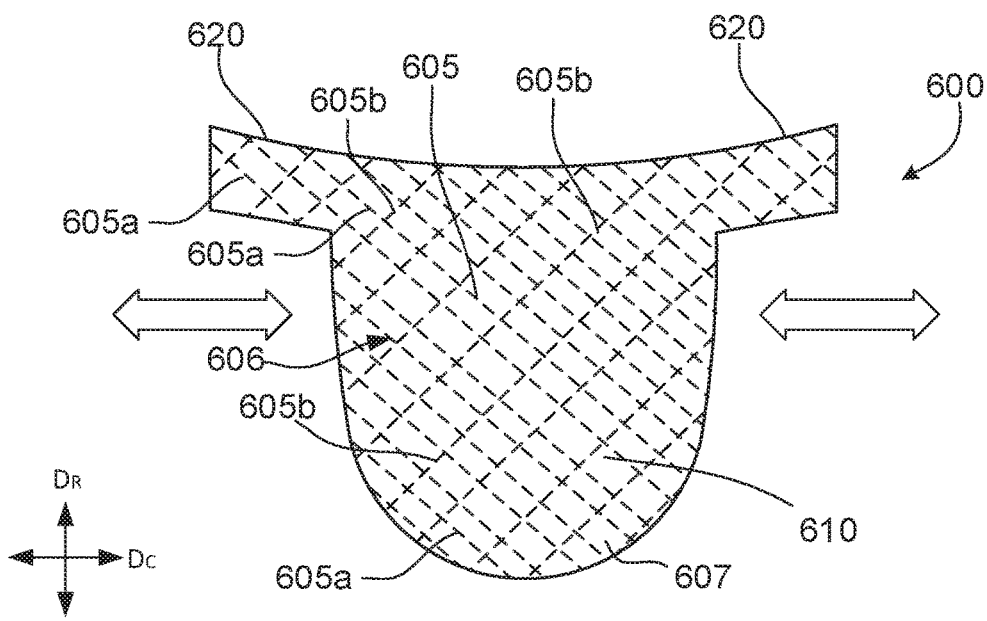

Referring to FIGS. 5 and 6, alternative embodiments of a prosthetic heart valve leaflet 500, 600 provided herein can include a composite material containing a plurality of reinforcement elements 505, 605 arranged as a mesh 506, 606 (depicted by dotted lines in the figures). The pre-stressed reinforcement elements 505, 605 can, in some cases, include a plurality of pre-stressed fibers, or wires, that are arranged to form a mesh, screen, or a fabric. Accordingly, in some cases, the prosthetic heart valve leaflets provided herein can include a pre-stressed mesh, screen, or fabric disposed within a polymer substrate 507, 607 (e.g., one or more polymer layers). A mesh 506, 606 can include a material containing a network of pre-stressed fibers, or wires, in which the individual fibers, or the wires, are randomly oriented, aligned in a pattern, or both. A fabric, which can be a subset of a mesh, is a material containing woven or knitted pre-stressed fibers or wires. A screen, which also can be a subset of a mesh, can include a material with a generally uniform thickness that contains a plurality of intersecting elongate members fused together at each intersection. In some cases, a prosthetic heart valve leaflet 500, 600 pro-vided herein can include a mesh, screen, or fabric that has been pre-stressed in its entirety, or in select areas.

The mesh 506, 606 can be at least partially embedded within polymeric layers 507, 607 of the leaflet 500, 600. In some cases, the polymer layers 507, 607 can include one or more polymeric layers (e.g., polymeric layers 408, 409 of FIG. 4B), such as a first polymeric layer and a second polymeric layer, in which the mesh 506, 606 is at least partially disposed between the first and second polymeric layers.

Referring specifically to FIG. 5, the depicted leaflet 500 includes a mesh 506 containing circumferentially-directed pre-stressed reinforcement elements 505a and radially-directed pre-stressed reinforcement elements 505b. The circumferentially-directed and radially-directed pre-stressed reinforcement elements 505a, 505b extend in a circumferential direction $D_C$ and a radial direction $D_R$, respectively, across a body portion 510 and two sleeve portions 520. In some cases, leaflet 500 provided herein can include the mesh 506 such that the circumferentially-directed reinforcement elements 505a are in greater or lesser tension (or compression) than the radially-directed reinforcement elements 505b. For example, in some cases, circumferentially-directed reinforcement elements 505a can be pre-stressed with a tensile force (or compression force) that is about 1%, about 2%, about 3%, about 5%, about 10%, about 20%, about 30%, about 40%, about 50%, about 60%, about 70%, about 80%, about 90%, about 100%, or more than 100% greater than the tensile force (or compression force) applied to the radially-directed reinforcement elements 505b.

Referring specifically to FIG. 6, the depicted leaflet 600 includes the mesh 606 containing a first set of pre-stressed reinforcement elements 605a and a second set of pre-stressed reinforcement elements 605b. The first and second sets of the pre-stressed reinforcement elements 605a, 605b are arranged at an angle oblique to the radial and circumferential directions $D_R$, $D_C$ of the leaflet. In some cases, as shown in FIG. 6, the first and second pre-stressed reinforcement elements 605a, 605b can extend in directions that are generally orthogonal to one another. In some cases, the first and second pre-stressed reinforcement elements 605a, 605b can extend in directions that are generally oblique to one another. In some cases, the leaflet 600 provided herein can include the mesh 606 that is pre-stressed in a direction that is parallel to the first set of the pre-stressed reinforcement elements 605a, the second set of the pre-stressed reinforcement elements 605b, or both. In some cases, the leaflet 600 provided herein can include the mesh 606 that is pre-stressed in an oblique direction relative to the first and second sets of the pre-stressed reinforcement elements 605a, 605b, as depicted by the arrows shown in FIG. 6.

In some cases, heart valve leaflets provided herein can include multiple layers of reinforcement elements (e.g., one or more fibers, meshes or fabric), in which at least a portion of one or more layers are pre-stressed. In some cases, a leaflet provided herein can include multiple layers of reinforcement elements (pre-stressed or non-stressed) that overlap one another, or are positioned adjacent to one another. For example, a leaflet provided herein can include a first mesh layer that is pre-stressed and a second mesh layer that is not tensioned, in which both the first and second mesh layers are at least partially disposed between at least two polymer layers. In some cases, heart valve leaflets provided herein can include two or more mesh layers of pre-stressed reinforcement elements in which a first mesh layer of the pre-stressed reinforcement elements contain a different material than a second mesh layer of the pre-stressed reinforcement elements. In some cases, the heart valve leaflets provided herein can include one, two, three, four, five, six, seven, eight, nine, ten, or more than ten mesh layers of reinforcement elements, in which one or more layers can be pre-stressed.

The leaflets provided herein can include pre-stressed reinforcement elements that are scalable to a range of sizes. In various cases, pre-stressed reinforcement elements (or layers) and polymer layers can be sized to construct a leaflet that has a thickness ranging from about 0.002 inches (50.8 micrometers) to about 0.005 inches (127 micrometers), including all values and ranges there between.

The dimension (e.g., a diameter or a width) of a pre-stressed reinforcement element, in some cases, can range from 0.0001 inches (2.54 micrometers) from about 0.0005 inches (12.7 micrometers), from about 0.0005 inches (12.7 micrometers) to about 0.001 inches (25.4 micrometers), from about 0.001 inches (25.4 micrometers) to about 0.002 inches (50.8 micrometers), from about 0.002 inches (50.8 micrometers) to about 0.003 inches (76.2 micrometers), from about 0.003 inches (76.2 micrometers) to about 0.004 inches (102 micrometers), or from about 0.004 inches (102 micrometers) to about 0.005 inches (127 micrometers).

In some cases, the thickness of a pre-formed polymer layers (e.g., a polymeric film or layer before being compressed into a leaflet form) can range from about 0.001 inches (25.4 micrometers) to about 0.002 inches (50.8 micrometers), from about 0.002 inches (50.8 micrometers) to about 0.003 inches (76.2 micrometers), from about 0.003 inches (76.2 micrometers) to about 0.004 inches (102 micrometers), or from about 0.004 inches (102 micrometers) to about 0.005 inches (127 micrometers).

FIGS. 7-13 show cross-sectional views of different embodiments of a reinforcement element. The prosthetic heart valve leaflet provided herein can contain one or more reinforcement elements including a cross-sectional shape, as desired. Suitable cross-sectional shapes include, but are not limited to, a circular (FIG. 7) shape, or a polygonal shape, such as a rectangular (FIG. 8), a square (FIG. 9), octagonal (FIG. 10), or triangular (FIG. 11) shape. In some cases, reinforcement elements can include features such as radiating spikes (FIG. 12), barbs, or hair-like extensions (FIG. 13) for increasing a mechanical bond between a reinforcement element and a surrounding polymer substrate (e.g., one or more polymer layers).

FIG. 14 provides another embodiment of a prosthetic heart valve 1400 provided herein. Prosthetic heart valve 1400 includes a base 1412 defining a substantially cylindrical passage 1413 and a plurality of polymeric leaflets 1414 disposed along the substantially cylindrical passage 1413. Each polymeric leaflet 1414 includes a respective root portion 1416 coupled to base 1412 and a respective edge portion 1418 movable relative to the root portion 1416 to coapt with the edge portions of the other polymeric leaflets along a coaptation region. In some cases, the entire heart valve 1400 can include a composite material provided herein. In some cases, portions of heart valve 1400, e.g., the polymeric leaflets 1414 of the heart valve 1400, may include the composite materials discussed herein. In some cases, the polymeric leaflets 1414 provided herein can include materials containing pre-stressed reinforcement elements, such as the pre-stressed fibers discussed herein.

Base 1412 includes a frame 1422 disposed in a polymer layer 1424. The polymer layer 1424 can be composed of composite materials provided herein. In some cases, polymer layer 1424 can include materials containing pre-stressed reinforcement elements, such as pre-stressed fibers. Polymer layer 1424 secures respective root portions 1416 of polymeric leaflets 1414 to the base 1412. Polymer layer 1424 can form a substantially continuous surface with respective root portions 1416 of polymeric leaflets 1414. This can reduce the likelihood of stress concentrations at the junction of respective root portions 1416 and base 1412. Additionally or alternatively, polymer layer 1424 can be disposed between each of polymeric leaflets 1414 and frame 1422 such that polymer layer 1424 protects polymeric leaflets 1414 from inadvertent contact with frame 1422 (e.g., as can occur through eccentric deformation of prosthetic heart valve 1400 on a calcium deposit present at the implantation site).

In some cases, frame 1422 is substantially cylindrical such that the outer surface of the base 1412 is substantially cylindrical and the polymer layer 1424 disposed on the frame 1422 forms the substantially cylindrical passage 1413. In some cases, frame 1422 is completely disposed in the polymer layer 1424, with the polymer layer 1424 forming a contoured outer surface of the valve 1400. In some cases, the frame 1422 is partially disposed in the polymer layer 1424. In some cases, the polymer layer 1424 is applied to the frame 1422 to form a substantially smooth inner and/or outer surface of the valve 1400.

Although the prosthetic heart valves provided herein are generally made of synthetic materials, such as materials that include pre-stressed reinforcement elements, such as pre-stressed fibers. In some cases, prosthetic heart valves can be made of both synthetic materials and non-synthetic materials such as animal tissue. For example, in some cases, at least a portion of a leaflet provided herein can be made from materials containing pre-stressed reinforcement elements, such as pre-stressed fibers, as well as tissue obtained from an animal, e.g., bovine pericardium or porcine tissue.

Methods of Forming Composite Materials Including Pre-stressed Reinforcement Elements A prosthetic heart valve provided herein and components thereof, e.g., heart valve leaflets, can be made using a wide variety of manufacturing processes. In some cases, processes that can be used for making the heart valves provided herein can include, but are not limited to, compression molding, dip coating, injection molding, extrusion, additive manufacturing, and combinations thereof.

In some cases, a method of manufacturing a prosthetic heart valve leaflet provided herein includes orienting a reinforcement element (e.g., a reinforcement fiber) between first and second polymer layers, pre-stressing the reinforcement element by applying an axial force (or a compression force) to the reinforcement element, and coupling the reinforcement element to the first and second polymer layers. In some cases, orienting the reinforcement element includes aligning the reinforcement element in a circumferential or a radial direction of a heart leaflet (e.g., the circumferential or radial direction shown on leaflet 300 of FIG. 3). In some cases, a method of manufacturing the leaflet provided herein includes dip coating one or more pre-stressed reinforcement elements.

Figure 15A:
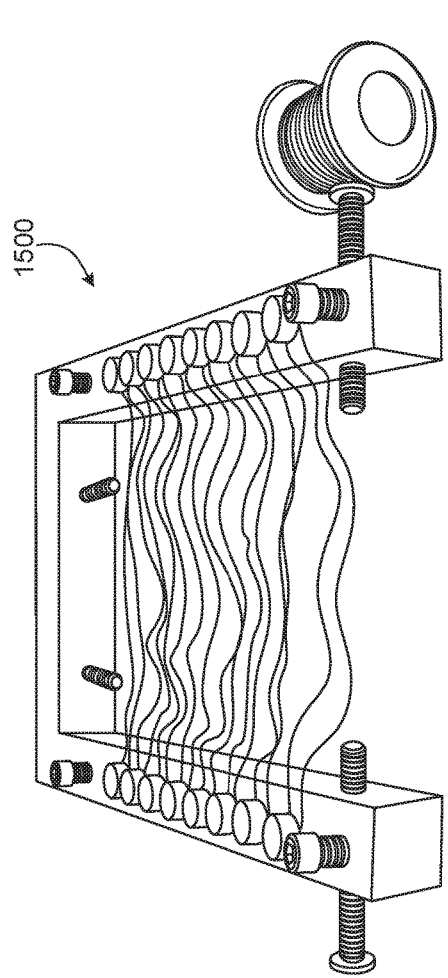
FIGS. 15A and 15B are perspective views of an exemplary tensioning fixture for forming a heart valve leaflet provided herein.
Figure 15B:
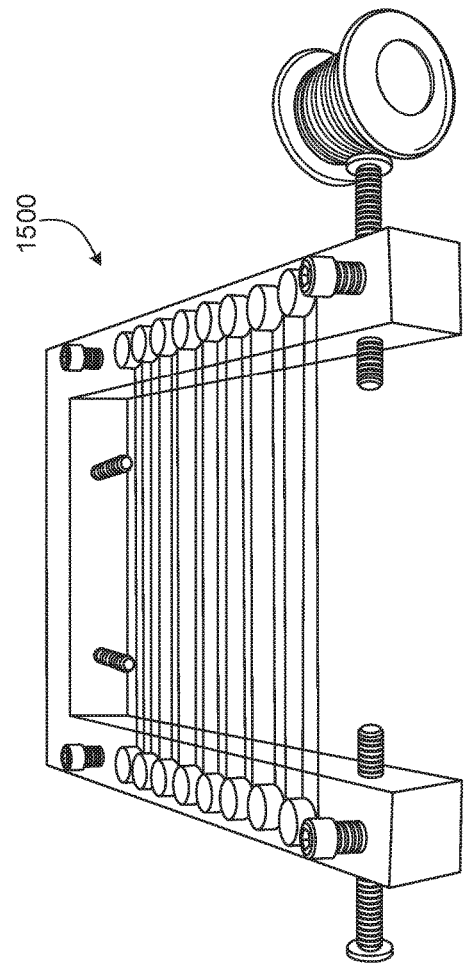

Pre-stressed reinforcement elements (e.g., pre-stressed fibers) of a composite material used to construct a heart valve can be pre-tensioned (or pre-compressed) to a range of axial (e.g., tensile or compressional) forces, as desired. In some cases, the pre-stressed reinforcement elements can be subjected to a predetermined tensile force. In various cases, the predetermined axial force can be applied to the reinforcement element (e.g., one or more reinforcement fibers) during manufacturing. In some cases, a tensile force or a compression force can be applied to the reinforcement element. In some cases, reinforcement elements (e.g., fibers)

can be mounted into a tensioning fixture, for example, a tensioning fixture 1300 as shown in FIGS. 15A and 15B. In some cases, the reinforcement element(s) can be fastened into the fixture, for example, by the use of a fastener, such as a screw (as shown in FIGS. 15A and 15B), compression rollers, adhesive, and the like. In some cases, a tensile force or a compression force ranging from about 0.25 pound-force (lbf) to about 10 lbf, including all values and ranges therebetween, may be applied to the reinforcement element. For example, pre-stressed reinforcement elements can be subjected to a tensile (or compression) load of about 0.1 lbf to about 0.2 lbf (or about 0.44 newtons (N) to about 0.89 N), from about 0.2 lbf to about 0.3 lbf (or about 0.9 N to about 1.3 N), from about 0.3 lbf to about 0.4 lbf (or about 1.3 N to about 1.8 N), from about 0.4 lbf to about 0.5 lbf (or from about 1.8 N to about 2.2 N), from about 0.5 lbf to about 1 lbf (or about 2.2 N to about 4.4 N), from about 1 lbf to about 2 lbf (or about 4.5 N to about 9 N), from about 2 lbf to about 3 lbf (or about 9 N to about 13 N), from about 3 lbf to about 4 lbf (or about 13 N to about 18 N), from about 5 lbf to about 7 lbf (or about 22 N to about 31 N), and from about 7 lbf to about 10 lbf (or about 31 N to about 44 N), in relation to a surrounding polymer layers that is in non-stressed state. In some cases, the reinforcement element is tensioned by elastically deforming the reinforcement element until the first and second layers have been coupled to the reinforcement element.

Various manufacturing processes and equipment can be used for applying axial force on a pre-stressed reinforcement element (e.g., one or more fibers). For example, in some cases, a tensioning fixture that can grasp a reinforcement element in two different locations and apply an axial force to the reinforcement element.

Figure 16:
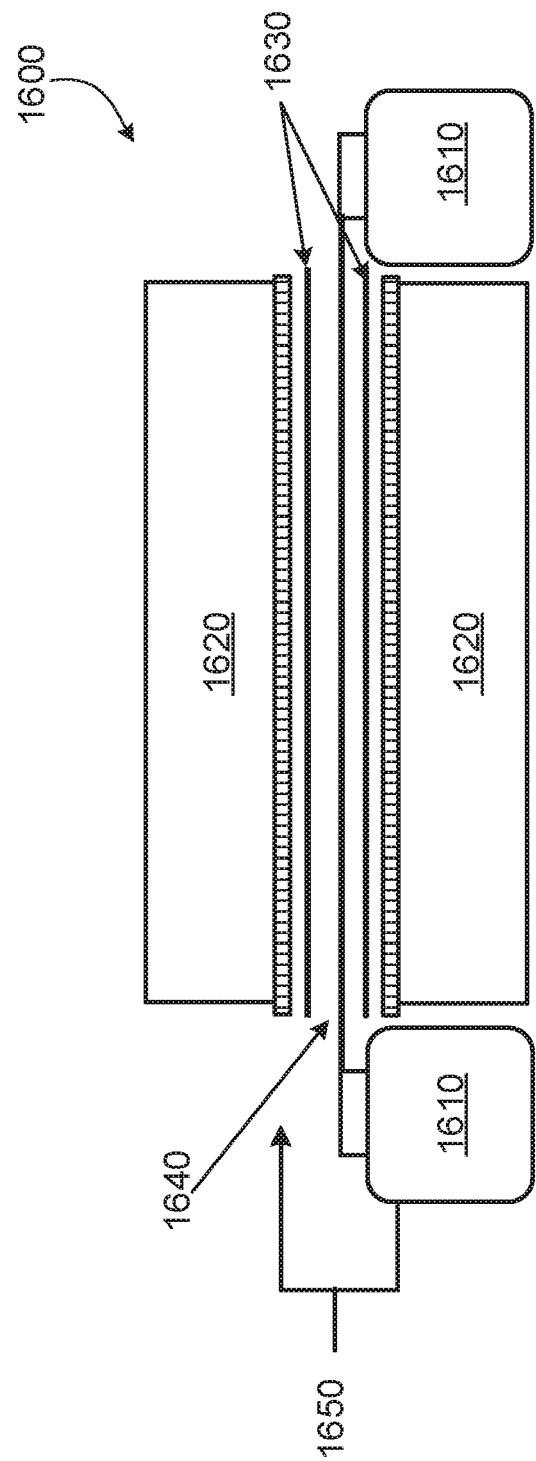
FIG. 16 is a perspective view of an exemplary process setup for forming a heart valve leaflet provided herein.

Various processes can be used to couple the reinforcement element (e.g., reinforcement fiber) to the first and second layers. Referring to FIG. 16, manufacturing assembly 1600 may include a tensioning fixture 1610 that is used in conjunction with a compression molding machine 1620 for forming the heart valve leaflets provided herein. In some cases, first and second polymeric layers 1630 are coupled to at least one reinforcement element 1640 (e.g., pre-stressed fibers or mesh) by compression molding the first and second layers 1630 to the reinforcement element 1640. In some cases, a non-stick substrate 1650, such as a Teflon sheet, can be placed between each polymeric layer 1630 and portions of the compression molding machine 1620 that come into contact with the polymeric layers to prevent sticking therebetween. The compression molding machine 1620 can apply heat to the reinforcement element 1640 and one or more polymeric layers 1630 for a pre-determined time to reflow the layers around the reinforcement element and/or bond the reinforcement element to the layers. For example, in some cases, a compression molding machine 1620 can apply heat to the subassembly for at least 5 minutes, 10 minutes, 20 minutes, 30 minutes, 45 minutes, 60 minutes, or greater than 60 minutes. Suitable compression molding temperatures can include a temperature range of about 300° F. (149° C.) to about 500° F. (260° C.) (e.g., from about 350° F. (177° C.) to about 400° F. (204° C.), from about 400° F. (204° C.) to about 450° F. (232° C.), from about 450° F. (232° C.) to about 500° F. (260° C.), from about 350° F. (177° C.) to about 450° F. (232° C.), from about 350° F. (177° C.) to about 500° F. (260° C.), or from about 400° F. (204° C.) to about 500° F. (260° C.)).

It should be understood that one or more design features of the heart valve devices provided herein can be combined with other features of other heart valve devices provided herein. In effect, hybrid designs that combine various features from two or more of the heart valve device designs provided herein can be created, and are within the scope of this disclosure.

While this specification contains many specific implementation details, these should not be construed as limitations on the scope of any invention or of what may be claimed, but rather as descriptions of features that may be specific to particular embodiments of particular inventions. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

In addition to being directed to the teachings described above and claimed below, devices and/or methods having different combinations of the features described above and claimed below are contemplated. As such, the description is also directed to other devices and/or methods having any other possible combination of the dependent features claimed below.

Numerous characteristics and advantages have been set forth in the preceding description, including various alternatives together with details of the structure and function of the devices and/or methods. The disclosure is intended as illustrative only and as such is not intended to be exhaustive. It will be evident to those skilled in the art that various modifications may be made, especially in matters of structure, materials, elements, components, shape, size and arrangement of parts including combinations within the principles of the invention, to the full extent indicated by the broad, general meaning of the terms in which the appended claims are expressed. To the extent that these various modifications do not depart from the spirit and scope of the appended claims, they are intended to be encompassed therein. All references, publications, and patents referred to herein, including the figures and drawings included therewith, are incorporated by reference in their entirety.

I claim:

1. A prosthetic heart valve, comprising:
a base; and
one or more heart valve leaflets, at least a portion of the leaflet comprising a composite material that includes a polymer substrate and a pre-stressed reinforcement element at least partially disposed in the polymer substrate,
wherein the pre-stressed reinforcement element is subject to a tensile force or compressive force of 0.1 pound-force to 10 pound-force when coupled to the polymer substrate.

2. The prosthetic heart valve of claim 1, wherein the pre-stressed reinforcement element is bonded to the polymer substrate at two or more discrete locations along a length of the pre-stressed reinforcement element.

3. The prosthetic heart valve of claim 1, wherein the polymer substrate and the pre-stressed reinforcement element comprise different materials.

4. The prosthetic heart valve of claim 1, wherein the polymer substrate comprises at least two polymer layers and the pre-stressed reinforcement element is disposed between the at least two polymer layers.

5. The prosthetic heart valve of claim 1, wherein the pre-stressed reinforcement element comprises a metal.

6. The prosthetic heart valve of claim 5, wherein the pre-stressed reinforcement element comprises nitinol.

7. The prosthetic heart valve of claim 1, wherein the pre-stressed reinforcement element comprises a polymer.

8. The prosthetic heart valve of claim 7, wherein the pre-stressed reinforcement element comprises polyetheretherketone (PEEK) or polyethersulfone (PES).

9. The prosthetic heart valve of claim 1, wherein the polymer substrate comprises polyisobutylene polyurethane (PIB-PUR).

10. The prosthetic heart valve of claim 1, wherein the pre-stressed reinforcement element is configured to be in tension when the polymer substrate is in a non-strained state.

11. The prosthetic heart valve of claim 1, wherein the pre-stressed reinforcement element is configured to be in tension, and at least a portion of the polymer substrate is configured to be in compression.

12. The prosthetic heart valve of claim 1, wherein the pre-stressed reinforcement element comprises a plurality of fibers.

13. The prosthetic heart valve of claim 1, wherein the pre-stressed reinforcement element comprises a mesh.

* * * * *